United States Patent [19]
See

[11] Patent Number: 5,747,464
[45] Date of Patent: May 5, 1998

[54] DIETARY SUPPLEMENT INCORPORATING β-SITOSTEROL AND PECTIN

[75] Inventor: Jackie Ray See, Fullerton, Calif.

[73] Assignee: Bio-Sphere Technology, Inc., Reno, Nev.

[21] Appl. No.: 685,209

[22] Filed: Jul. 23, 1996

Related U.S. Application Data

[63] Continuation of Ser. No. 430,136, Apr. 26, 1995, abandoned, which is a continuation of Ser. No. 83,340, Jun. 25, 1993, abandoned.

[51] Int. Cl.$^6$ ............ A61K 31/705; A61K 31/715; C08B 37/06
[52] U.S. Cl. ............ 514/26; 514/54; 514/824; 536/18.5; 536/115; 536/123.1; 536/2
[58] Field of Search ............ 514/26, 54, 824; 536/18.5, 18.6, 115, 123.1, 2

[56] References Cited

U.S. PATENT DOCUMENTS

| | | | |
|---|---|---|---|
| 3,881,005 | 4/1975 | Thakkar et al. | 424/238 |
| 4,865,850 | 9/1989 | Shell et al. | 424/491 |
| 5,112,815 | 5/1992 | Ambrus et al. | 514/178 |
| 5,244,887 | 9/1993 | Straub | 514/182 |
| 5,277,910 | 1/1994 | Hidvegi | 424/195.1 |
| 5,384,400 | 1/1995 | Crescenzi et al. | 536/2 |

OTHER PUBLICATIONS

*Carbohydrate Chemistry*, Ed. John F. Kennedy, Clarendon Press, pp. 233–235 & 620–622, (1988).

Oster et al., *Dtsch. Med. Wschr.*, vol. 101/36, pp. 1308–1311, (1976) Abstract only.

Pirich et al., *Wien Klin. Wochenschr.*, vol. 104(11), pp. 314–316, (1992) Abstract only.

Sable–Amplis et al., *Med. Sci. Res.*, vol. 16(9), pp. 453–454, (1988) Abstract only.

Lu et al. *Nutritional Research* (N.Y.) vol. 9(3): 345–352, (1989).

Vanhanen, H. et al., Effects of Sitostanol Ester, Dissolved in Dietary Oil, on Serum Cholesterol, Plant Sterols and Cholesterol Precursors, Second Department of Medicine, University of Helsinki, Helsinki, Finland, Circulation Supplement II, Abstracts From the 64th Scientific Sessions, 2389, Oct. 91.

Nicolosi, R.J., Beyond Fatty Acids, Department of Clinical Sciences, University of Massachusetts Lowell, Lowell, MA 01854, Circulation, vol. 85, No. 2, Feb. 1992.

Haskell, W. L., Role of Water–Soluble Dietary Fiber in the Management of Elevated Plasma Cholesterol in Healthy Subjects, The American Journal of Cardiology, Feb. 15, 1992, vol. 69, No. 5, pp. 433–437.

Hospital Pharmacology Goodman and Gilman: The Pharmacological Basis of Therapeutics 7th Edition, 1985, p. 843.

Briones, Esperanza R., Primary Hypercholesterolemia: Effect of Treatment on Serum Lipids, Lipoprotein Fractions, Cholesterol Absorption, Sterol Balance, and Platelet Aggregation, Mayo Clin Proc, Apr. 1984, vol. 59, pp. 251–257.

Kane, John P. et al., Treatment of Hypercholesterolemia, Medical Clinics of North America—vol. 66, No. 2, Mar. 1992, pp. 537–550.

Merck Manual, Skimmin, 1983, p. 1227.

Gundy, Scott M. et al., Colestipol, clofibrate, and phytosterols in combined therapy of hyperlipidemia, J. Lab. Clin Med, Feb. 1977, pp. 354–366.

Strocchi, Alessandra, et al., An understanding of absorptive physiology facilitates prompt recognition of signs and symptoms of malabsorption, use and interpretation of diagnostic tests, and selection of specialized tests to determine the etiology, Contemporary Internal Medicine, Apr. 1992, pp. 91–110.

Ripsin, Cynthia M., et al., Oat Products and Lipid Lowering, JAMA, Jun. 24, 1992–vol. 267, No. 24, pp. 3317–3325.

Cerda, J.J. et al., The Effects of Grapefruit Pectin and Patients at Risk for Coronary Heart Disease Without Altering Diet or Lifestyle, Clin. Cardiol. vol. 11, pp. 589–594 (1988).

Baekey, P.A. et al., Grapefruit Pectin Inhibits Hypercholesteroleima and Atherosclerosis in Miniature Swine, Clin. Cardiol. vol. 11, pp. 595–600 (1988).

*Primary Examiner*—John Kight
*Assistant Examiner*—Howard C. Lee
*Attorney, Agent, or Firm*—Christie, Parker & Hale, LLP

[57] ABSTRACT

A composition for inhibiting absorption of fat and cholesterol from the gut and a method for making and using the composition. The composition comprises β-sitosterol bound irreversibly to pectin to form a β-sitosterol/pectin complex.

18 Claims, No Drawings

DIETARY SUPPLEMENT INCORPORATING β-SITOSTEROL AND PECTIN

This is a continuation of application Ser. No. 08/430,136, filed Apr. 26, 1995 (now abandoned) which is a continuation of application Ser. No. 08/083,340, filed Jun. 25, 1993 (now abandoned).

FIELD OF THE INVENTION

This invention relates to a composition and method for the reduction of serum cholesterol and weight reduction.

BACKGROUND OF THE INVENTION

Cholesterol is an essential molecule in animals, required for the synthesis of cell membranes and as a precursor of steroid hormones and bile salts. However, high levels of serum cholesterol, especially low density lipoprotein (LDL), and serum lipids have been correlated with an increased risk of coronary heart disease. Deposition of lipid plaques on the intima of arteries (atheroma), resulting in atherosclerosis, appears to occur most readily when serum lipids are elevated in concentration.

The average diet in the United States provides about 40 percent of calories as lipids and approximately 57% of adult Americans have borderline high cholesterol (greater than 200 mg/dl). Coronary heart disease constitutes a leading cause of mortality and morbidity in the United States. Its principle underlying cause, atherosclerosis, is responsible for a large percentage of deaths and disabilities.

Dietary management is generally recommended to lower total and LDL cholesterol concentrations by reducing the intake of saturated fats and cholesterol and weight reduction for those overweight, by eliminating excess calories. However, many people at moderate to high risk for coronary heart disease are unwilling to change to a low risk diet or find that such a change is not feasible. As an alternative several medications and dietary supplements such as cholestyramine resin, probucol, colestipol HCl, nicotinic acid, mevinolin, pectin, guar gum and oat bran have been proposed for use to control serum cholesterol levels. However, for the most part these medications are unpleasant to take and may have undesirable side effects. Brans and fibers as dietary supplements must be taken in large volumes to be minimally effective. Even if these dietary supplements are effective in reducing serum cholesterol they will not affect weight reduction unless fat intake is limited.

Another naturally occurring compound reported to be effective in lowering serum cholesterol is a plant steroid, β-sitosterol. β-sitosterol has been shown to impair adsorption of cholesterol. However the compound can be absorbed and result in xanthomatous deposits and can have an estrogen like activity.

There is a need for a dietary supplement which lowers cholesterol, especially low density lipoprotein, by altering dietary fat and cholesterol absorption. Such a supplement should be palatable and non-toxic for extended use.

SUMMARY OF THE INVENTION

A composition for inhibiting absorption of fat and cholesterol from the gut is described. The composition comprises β-sitosterol bound irreversibly to pectin to form a β-sitosterol/pectin complex.

The β-sitosterol/pectin complex is prepared by a method comprising mixing β-sitosterol and pectin and suspending the β-sitosterol/pectin mixture in water. The suspension is then heated to complex β-sitosterol and pectin and then acidified. The acidified β-sitosterol/pectin is then heated to form a β-sitosterol/pectin complex.

The composition is useful for weight reduction when administered to a patient desiring a reduction in body weight and for reducing serum cholesterol levels in a patient suffering from elevated serum cholesterol.

DETAILED DESCRIPTION

The present invention relates to a complex of pectin and β-sitosterol. The compounds are each known to be effective in reducing cholesterol, however, to be effective they are required in large quantities. Also β-sitosterol has toxic or at least undesirable side effects.

β-sitosterol is derived from soy and rice and has a structure similar to cholesterol, except for the substitution of an ethyl group at C-24 of its side chain. Pectin is a polysaccharide derived primarily from citrus rind. It has a molecular weight of 20,000–40,000, of partial methyl ester of $\alpha$-(1→4) linked D-galacturonate sequences interrupted with (1→2)-L-rhamnose residues. Neutral sugars, D-galactose, L-arabinose, D-xylose and L-fructose, form side chains of the pectin molecule. Pectin is not broken down by enzymes of the gastrointestinal tract and is, therefore, a dietary fiber.

For use in the present invention pectin is irreversibly complexed with β-sitosterol to form a complex which is not degraded by pH changes or enzymes of the gut, thus rendering the β-sitosterol non-absorbable by the gut.

To prepare the β-sitosterol/pectin complex, about 300 mg of β-sitosterol (Sigma Chemical Co. of St Louis Mo., Cat. No. S9889) is mixed with about 30 mg pectin (Sigma Chemical Co., Cat. No. P2157) the mixture is dried at room temperature for about five minutes. About 30 ml of distilled water is added to the mixture and the suspension is stirred at room temperature for about 5 minutes to hydrate the β-sitosterol and pectin. The suspension is then heated at about 93° C. for about 2 minutes to complex the β-sitosterol with the pectin. The complexed suspension is then cooled at room temperature for about 5 minutes and acidified by the addition of about 15 ml of rice wine vinegar (4.3% v/v acetic acid). The acidified complex is stirred at room temperature for about 5 minutes, heated at about 93° C. for about 6 minutes and then sized by pushing the acidified suspension through a 20 mesh sieve.

Excipients are then added. About 335 mg of calcium carbonate and about 2 ml of water are added and the mixture stirred at about 40° C. for about 10 minutes. About 18 mg of calcium silicate, about 18 mg of silicon dioxide and about 18 mg of croscarmellose sodium are then added and the mixture is stirred at about 40° C. for about 10 minutes. About 10 mg of magnesium stearate is then added and the mixture is stirred for about 5 minutes. The mixture is pressed into about a 700 mg tablet with about 20,000 psi pressure.

One tablet of about 700 mg is taken about 30 minutes before a meal.

EXAMPLE 1

300 mg of β-sitosterol was mixed with 30 mg pectin and dried at room temperature for five minutes. 30 ml of distilled water was added to the mixture and the resultant suspension was stirred at room temperature for 5 minutes to hydrate the β-sitosterol and pectin. The suspension was then heated at 93° C. for 2 minutes to complex the β-sitosterol with the pectin. The complexed suspension was cooled at room temperature for 5 minutes and acidified by the addition of 15 ml of rice wine vinegar. The acidified complex was stirred at room temperature for 5 minutes, heated at 93° C. for 6 minutes and sized by pushing the β-sitosterol/pectin complex through a 20 mesh sieve.

334 mg of calcium carbonate and 2 ml of water were added and the mixture was stirred at 40° C. for 10 minutes. 18 mg of calcium silicate, 18 mg of silicon dioxide and 18 mg of croscarmellose sodium were then added and the mixture was stirred at 40° C. for 10 minutes. 10 mg of magnesium stearate was then added and the mixture was stirred for an additional 5 minutes. The resultant mixture was pressed into 727 mg tablet with 20,000 psi pressure.

The resultant pill was placed in distilled water, pH 7, and broke down to a soft, whitish, pleasant smelling flocculent within 30 minutes.

EXAMPLE 2

Pills prepared as described in Example 1 were crushed and suspended in 100 ml of distilled water, adjusted to pH 3 with acetic acid. The suspension was heated at 36° C. for 30 minutes with vigorous agitation. The suspension was then cooled for 5 minutes and a suspension sample was collected. The remaining suspension was filtered through 100 micron filter paper and the filtrate collected. The suspension sample and the filtrate were analyzed by infrared Fourier resonance spectroscopy (IFRS). Samples were also dried and the residue weight determined. Solutions of β-sitosterol alone, pectin alone and an uncomplexed mixture of β-sitosterol and pectin where used for comparison in the IFRS analysis.

The dry weight of the β-sitosterol/pectin complex and the filtrate indicated that less than 1% w/w of the complex was solubilized by the solubilization conditions at pH 3. The IFRS analysis indicated that the β-sitosterol/pectin complex retained double and single carbon-carbon bonds different from either β-sitosterol and pectin.

The pH of the stomach is normally about pH 3, therefore, the β-sitosterol/pectin complex retains its structure and is expected to pass through the stomach intact.

EXAMPLE 3

Pills prepared as described in Example 1 were crushed and suspended in 100 ml of distilled water, adjusted to pH 11 with sodium hydroxide. The suspension was heated at 36° C. for 60 minutes with vigorous agitation. The suspension was cooled for 5 minutes and a suspension sample was collected. The remaining suspension was filtered through 100 micron filter paper and the filtrate collected. The suspension sample and the filtrate were analyzed by IFRS. Samples were also dried and the residue weight determined. Solutions of β-sitosterol alone, pectin alone and an uncomplexed mixture of β-sitosterol and pectin where used for comparison in the IFRS analysis.

The dry weight of the β-sitosterol/pectin complex and the filtrate indicated that about 50% w/w of the β-sitosterol/pectin complex was solubilized by the solubilization conditions at pH 11. The IFRS analysis indicated that the β-sitosterol/pectin complex retained double and single carbon-carbon bonds different from either β-sitosterol and pectin.

The pH of the distal small intestine is about pH 11. Therefore, the β-sitosterol/pectin complex is expected to be solubilized in the small intestine where it will be available for complexing cholesterol and fat receptors.

EXAMPLE 4

Five patients were given a 727 mg tablet, prepared as described in Example 1, about 30 minutes before each meal for two weeks. At the end of the two week period serum samples were obtained and analyzed for β-sitosterol by gas chromatography as described by Vanhanen et al., Circulation Supplement II, 2390, (1991), incorporated herein by reference.

No β-sitosterol was detected in the samples, indicating that β-sitosterol was not absorbed from the gut and remains complexed to the pectin.

EXAMPLE 5

Fourteen patients with mixed lipoproteinemia, on a diet of 500 mg of cholesterol/day, were given a 727 mg tablet of β-sitosterol/pectin complex, prepared as described in Example 1, about 30 minutes before each meal for eight weeks in a double blind, cross-over study. Total cholesterol, LDL and HDL were performed prior to beginning the administration of the β-sitosterol/pectin complex and at monthly intervals thereafter, were determined enzymatically in an enzyme linked assay using cholesterol esterase, cholesterol oxidase and peroxidase, by methods well known to those skilled in the art and as described in Sigma procedure No. 352 (Sigma Chemical Co., St Louis Mo.), incorporated herein by reference. Body weight was also determined. The results are set out in Tables I–IV.

TABLE I

| TOTAL CHOLESTEROL | | | | |
|---|---|---|---|---|
| "Normal" = 100-200[1] | Pre-Admin. | 1 Month Admin. | 2 Months Admin. | 3 Months Admin. |
| Average | 277 | 231 | 241 | 241 |
| Range | 192–352 | | | |

[1]mg/dl

After administration for 1 month a reduction of 16.4% was observed in the serum cholesterol of the patients in the study. A statistically significant reduction was maintained over three months.

TABLE II

| LDL CHOLESTEROL | | | | |
|---|---|---|---|---|
| "Normal" = > 130[1] | Pre-Admin. | 1 Month Admin. | 2 Months Admin. | 4 Months Admin. |
| Average | 223 | 157 | 175 | 156[2] |
| Range | 120–252 | 118–218 | 128–224 | |

[1]mg/dl
[2]results for 2 patients whose LDL cholesterol began at 389 mg/dl

A decrease of 15.2% was observed in LDL cholesterol levels of the patients in the study at 1 month and a statistically significant decrease was maintained over 4 months.

TABLE III

| HDL RATIOS | | | | |
|---|---|---|---|---|
| "Normal" = | Pre-Admin. | 1 Month Admin. | 2 Months Admin. | 4 Months Admin. |
| Average | 6.8 | 6.8 | 6.7 | 7.6[1] |

[1]for 3 patients

No significant difference was observed in the HDL ratio.

TABLE IV

BODY WEIGHT

|  | Pre-Admin. | 1 Month Admin. | 2 Months Admin. |
|---|---|---|---|
| Average | 82.1[1] | 86.6 | 76.2 |
| Range | 57.2–113.9 | 68.5–100.2 | 57.2–78 |

[1]kg

A body weight increase of 5.5% was observed after one month of administration of the β-sitosterol/pectin complex. However, after two months administration there was a decrease of 7.2% from the pre-administration average weight.

The patients in the study were also monitored for liver and kidney function and interference of the β-sitosterol/pectin complex with current medication. No change, during the course of the study, was attributed to the administration of the complex. Additionally, no adverse reactions such as nausea, vomiting, diarrhea, constipation, skin rash, headache, etc. were suffered by the patients during the period they were taking the β-sitosterol/pectin complex.

Therefore, the β-sitosterol/pectin complex is effective in reducing total cholesterol and LDL cholesterol. The β-sitosterol/pectin complex is also effective in body weight reduction.

EXAMPLE 6

Fat was tagged with retinoic acid and given to a patient with a measured meal, as described in See et al., Clinical Research (April, 1991) incorporated herein by reference. A second patient was given ox bile (cholic acid) in addition to the tagged fat and a third patient was given β-sitosterol/pectin complex prepared as described in Example 1, in addition to tagged fat, 30 minutes prior to the ingestion of the meal. The serum levels of the retinoic acid tag were determined for each patient at two hourly intervals. The results are summarized in Table V.

TABLE V

Retinoic Acid Absorption

|  | 0 | 2 hr. | 4 hr. | 6 hr. |
|---|---|---|---|---|
| Tagged Fat | 45[1] | 62 | 67 | 52 |
| Tagged fat + ox bile | 52 | 55 | 78 | 77 |
| Tagged fat + β-sitosterol/pectin | 38 | 47 | 43 | 42 |

[1]µg/dl retinoic acid

The results indicate that tagged fat is taken up and reaches a maximum in 2–4 hours after ingestion. By 6 hours the serum levels have dropped to about baseline. The addition of ox bile results in a greater increase in fat absorption and serum fat levels which remain at an elevated level after 6 hours. In contrast β-sitosterol/pectin complex results in a lower absorption of the retinoic acid tag, about half the amount absorbed when tagged fat was given alone, after two hours. By 4 hours the fat absorption had dropped to baseline indicating that β-sitosterol/pectin complex inhibits dietary fat absorption.

The present invention is not limited to the specific embodiment given. It will be obvious to one skilled in the art that other doses and timing of the dosage could be used to advantage to suit the needs of different individuals and that other excipients could be used. Therefore, the present invention is not intended to be limited to the working embodiments described above. The scope of the invention is defined in the following claims.

What is claimed is:

1. A composition for inhibiting absorption of fat and cholesterol from the gut, said composition comprising β-sitosterol and apple pectin combined to form a β-sitosterol/apple pectin complex, wherein said composition is substantially insoluble in the human stomach and capable of passing through the stomach substantially intact.

2. A composition as recited in claim 1 wherein β-sitosterol and apple pectin are present in a ratio of 10 β-sitosterol:1 apple pectin, by weight.

3. A composition as recited in claim 1 wherein the β-sitosterol/apple pectin complex is pressed into pills for oral administration.

4. A composition as recited in claim 3 wherein the pills further comprise an excipient.

5. A composition as recited in claim 4 wherein the excipient is selected for the group consisting of calcium carbonate, silicon dioxide, croscarmellose sodium, magnesium stearate and mixtures thereof.

6. A method for preparing a β-sitosterol/apple pectin complex comprising:

mixing β-sitosterol and apple pectin;

suspending the β-sitosterol/apple pectin mixture in water;

heating the suspension to form a β-sitosterol/pectin complex;

acidifying the β-sitosterol/apple pectin complex; and thereafter heating the β-sitosterol/apple pectin complex.

7. A method as recited in claim 6 wherein the β-sitosterol and apple pectin are mixed in a ration of 10 β-sitosterol:1 pectin, by weight.

8. A method as recited in claim 6 wherein the β-sitosterol/apple pectin mixture is suspended in 1 volume of water with respect to the weight of apple pectin.

9. A method as recited in claim 6 wherein the β-sitosterol and apple pectin suspension is heated at 93° C. to complex the β-sitosterol and apple pectin.

10. A method as recited in claim 6 wherein the complexed β-sitosterol and apple pectin is acidified by the addition of a 0.5 volume, with respect to the weight of pectin, of 4.3% acetic acid.

11. A method as recited in claim 6 wherein the acidified β-sitosterol and pectin is heated at 93° C.

12. A method as recited in claim 6 further comprising sizing the β-sitosterol/apple pectin complex by pushing the complex through a 20 mesh sieve.

13. A method for reducing serum cholesterol levels comprising orally administering a β-sitosterol/apple pectin complex composition to a human suffering from serum cholesterol levels which are elevated above normal levels for a human population, said composition being substantially insoluble in the human stomach and capable of passing through the human's stomach substantially intact.

14. A method as recited in claim 13 wherein the βsitosterol/apple pectin complex composition is administered orally to said human about 30 minutes before each meal.

15. A method as recited in claim 13 wherein the β-sitosterol/apple pectin complex composition is administered to said human in tablet form before each meal, wherein the tablet comprises about 300 mg of β-sitosterol and about 30 mg of apple pectin.

16. A composition for inhibiting absorption of fat and cholesterol from the gut comprising β-sitosterol and apple pectin made by the following process:

mixing together β-sitosterol and apple pectin;

suspending the β-sitosterol/apple pectin mixture in water;

heating the suspension to form a β-sitosterol/apple pectin complex;

acidifying the complexed β-sitosterol and apple pectin; and thereafter heating the β-sitosterol/apple pectin complex.

17. A composition according to claim 16, wherein the β-sitosterol/apple pectin complex is pressed into pills for oral administration.

18. A composition as recited in claim 16, wherein the β-sitosterol and apple pectin are present in a ratio of 10 β-sitosterol:1 apple pectin, by weight.

* * * * *

UNITED STATES PATENT AND TRADEMARK OFFICE
CERTIFICATE OF CORRECTION

PATENT NO. : 5,747,464
DATED : May 5, 1998
INVENTOR(S) : Jackie Ray See

It is certified that error appears in the above-indentified patent and that said Letters Patent is hereby corrected as shown below:

On the title page,
Item [56] References Cited, U.S. Patent Documents, under U.S. Patent Documents insert thefollowing references:
-- 4,602,003  7/1986  Malinow.....514/26
   4,602,005  7/1986  Malinow.....514/26 --.
Column 3, line 12, before "727 mg" insert -- a --.
Column 4, line 63, delete ""Normal=""
Column 5, line 40, change "hourly" to -- hour --.
Column 6, line 38, change "ration" to -- ratio --.
Column 6, line 51, after "β-sitosterol and" insert -- apple --.
Column 6, line 63, change "βsitosterol/apple" to --β-sitosterol/apple --.
Column 7, lines 5, 7, change "β -sitosterol" to -- β-sitosterol --
   (both occurrences).

Signed and Sealed this

Eleventh Day of May, 1999

Attest:

Q. TODD DICKINSON

*Attesting Officer*   *Acting Commissioner of Patents and Trademarks*